US010881765B2

(12) United States Patent
Igarashi

(10) Patent No.: US 10,881,765 B2
(45) Date of Patent: Jan. 5, 2021

(54) BLOOD COMPONENT COLLECTION SYSTEM WITH PRESSURE DETECTION APPARATUS HAVING TWO LOAD DETECTORS AND METHOD

(71) Applicant: TERUMO KABUSHIKI KAISHA, Tokyo (JP)

(72) Inventor: Masatsugu Igarashi, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/620,933

(22) PCT Filed: Apr. 20, 2018

(86) PCT No.: PCT/JP2018/016302
§ 371 (c)(1),
(2) Date: Dec. 10, 2019

(87) PCT Pub. No.: WO2018/230155
PCT Pub. Date: Dec. 20, 2018

(65) Prior Publication Data
US 2020/0197582 A1    Jun. 25, 2020

(30) Foreign Application Priority Data
Jun. 16, 2017   (JP) ................................. 2017-118849

(51) Int. Cl.
*A61M 1/02* (2006.01)
*A61M 1/36* (2006.01)
*B04B 11/04* (2006.01)

(52) U.S. Cl.
CPC .......... *A61M 1/025* (2013.01); *A61M 1/3672* (2013.01); *A61M 1/3693* (2013.01);
(Continued)

(58) Field of Classification Search
CPC .. A61M 1/025; A61M 1/3672; A61M 1/3693; A61M 2202/0415; A61M 1/38;
(Continued)

(56) References Cited

U.S. PATENT DOCUMENTS 6,491,656 B1 *  12/2002  Morris ................ A61M 1/3681
                                                         604/6.09
10,352,950 B2 *  7/2019  Ochiai ..................... C12Q 1/54
(Continued)

FOREIGN PATENT DOCUMENTS

EP        3228341 A1     10/2017
WO   WO-2004061399 A2 *  7/2004 .......... A61M 1/3639
(Continued)

*Primary Examiner* — Charles Cooley
(74) *Attorney, Agent, or Firm* — Terumo BCT, Inc IP Law Dept.

(57) ABSTRACT

A blood component collection cassette, kit, or system, and a flow path internal pressure detection method capable of accurately measuring a circuit internal pressure. A flow path formed in a cassette body has a first line through which blood flows when a blood component separation device is in operation, and a second line through which blood does not flow when the blood component separation device is in operation. The first line has a first pressure-receiving portion pressed by a first load detector. The second line has a second pressure-receiving portion pressed by a second load detector.

21 Claims, 14 Drawing Sheets

(52) U.S. Cl.
CPC ...... *B04B 11/04* (2013.01); *A61M 2202/0415* (2013.01); *A61M 2205/125* (2013.01); *A61M 2205/3327* (2013.01); *A61M 2205/3344* (2013.01); *A61M 2205/50* (2013.01); *A61M 2205/702* (2013.01); *A61M 2205/7545* (2013.01); *A61M 2207/00* (2013.01)

(58) Field of Classification Search
CPC .......... A61M 1/302; A61M 2205/3331; A61M 2205/70; A61M 1/3639; A61M 2205/50; A61M 2205/702; A61M 2205/7545; A61M 2207/00; A61M 2205/125; A61M 2205/3327; A61M 2205/3344; B04B 11/00; B04B 7/02; B04B 5/0442; B04B 11/04; B04B 5/0428; B04B 13/00
See application file for complete search history.

(56) References Cited

U.S. PATENT DOCUMENTS

| | | | | |
|---|---|---|---|---|
| 10,758,664 | B2 * | 9/2020 | Igarashi | .................. B04B 7/02 |
| 10,758,665 | B2 * | 9/2020 | Igarashi | ............. A61M 1/0218 |
| 10,773,013 | B2 * | 9/2020 | Igarashi | ................. B04B 13/00 |
| 10,780,212 | B2 * | 9/2020 | Igarashi | ................ B04B 11/04 |
| 2010/0152013 | A1 * | 6/2010 | Eberle | ................ A61M 1/3693 494/10 |
| 2010/0292628 | A1 * | 11/2010 | Powers | ............... A61M 1/3639 604/6.01 |
| 2016/0243300 | A1 * | 8/2016 | Nackaerts | ............... B04B 11/00 |
| 2019/0038197 | A1 * | 2/2019 | Igarashi | ........... A61B 5/150267 |
| 2019/0046710 | A1 * | 2/2019 | Kusters | .................. A61M 1/367 |
| 2019/0231949 | A1 * | 8/2019 | Igarashi | ............. A61M 1/0209 |
| 2019/0290822 | A1 * | 9/2019 | Igarashi | ............... B01D 21/262 |
| 2019/0290825 | A1 * | 9/2019 | Igarashi | .................... A61M 1/38 |
| 2019/0290830 | A1 * | 9/2019 | Igarashi | .................... B04B 3/00 |
| 2019/0290831 | A1 * | 9/2019 | Igarashi | ................ A61M 1/306 |
| 2020/0030505 | A1 * | 1/2020 | Igarashi | .................. B29C 49/20 |
| 2020/0164135 | A1 * | 5/2020 | Igarashi | ............. A61M 1/0259 |
| 2020/0164136 | A1 * | 5/2020 | Igarashi | .................. A61M 1/30 |
| 2020/0164137 | A1 * | 5/2020 | Igarashi | ................ B04B 5/0442 |
| 2020/0197582 | A1 * | 6/2020 | Igarashi | ................ A61M 1/302 |
| 2020/0197583 | A1 * | 6/2020 | Igarashi | .................. A61M 1/30 |
| 2020/0222614 | A1 * | 7/2020 | Igarashi | ............... A61M 1/3639 |
| 2020/0306442 | A1 * | 10/2020 | Igarashi | ............... A61M 1/3627 |
| 2020/0316282 | A1 * | 10/2020 | Igarashi | ............. A61M 1/0222 |
| 2020/0345906 | A1 * | 11/2020 | Igarashi | ............... A61M 1/3693 |

FOREIGN PATENT DOCUMENTS

| | | | |
|---|---|---|---|
| WO | 2004061399 A2 | 4/2007 | |
| WO | 1996040322 A2 | 5/2007 | |
| WO | WO-2018230155 A1 * | 12/2018 | .......... A61M 1/3693 |
| WO | WO-2018230156 A1 * | 12/2018 | ............ A61M 1/302 |
| WO | WO-2018230545 A1 * | 12/2018 | .......... A61M 1/0218 |

* cited by examiner

BLOOD COMPONENT COLLECTION SYSTEM WITH PRESSURE DETECTION APPARATUS HAVING TWO LOAD DETECTORS AND METHOD

TECHNICAL FIELD

The present invention relates to a blood component collection cassette, a blood component collection kit, a blood component collection system, and a flow path internal pressure detection method.

BACKGROUND ART

In blood donation of recent years, besides whole blood collection for collecting whole blood from a donor, component collection (apheresis) which is a light burden on a body of the donor has been carried out. Component collection is a blood collection method that uses a blood component collection system (apheresis system), collects only specific blood components from whole blood, and returns remaining components into the body of the donor again.

PTL 1 discloses a blood component collection system that collects platelets by centrifuging whole blood taken out of a donor. This blood component collection system includes a blood collection circuit set forming a circuit through which blood or blood components to be treated flow, and a centrifugal separator (blood component separation device) to which the blood collection circuit set is attached.

The blood collection circuit set includes a blood collection line having a blood collection needle, a strip-like channel (separator) into which whole blood is introduced, a plurality of bags for accommodating a blood component, etc., and a cassette connected thereto through a plurality of tubes. A plurality of flow paths including a line for introducing blood from the donor, a line for transferring blood components to a bag, a blood return line for returning blood components not collected to the donor, etc., are formed in the cassette. During use, the cassette is attached to an attaching portion provided in the blood component separation device.

CITATION LIST

Patent Literature

[PTL 1]
JP 2013-514863 A

SUMMARY OF INVENTION

Technical Problem

In such a blood component collection system, it is necessary to measure and monitor a pressure (circuit internal pressure) in the blood collection circuit in order to check whether the blood component separation device is properly operating. It is desirable that both a negative pressure and a positive pressure can be measured as the circuit internal pressure, and accurate measurement is allowed even in a low pressure region.

The present invention has been made in view of the above problems, and an object thereof is to provide a blood component collection cassette, a blood component collection kit, a blood component collection system, and a flow path internal pressure detection method capable of accurately measuring a circuit internal pressure in negative pressure and positive pressure regions.

Solution to Problem

To achieve the above-mentioned object, the present invention is a blood component collection cassette including a cassette body in which a flow path is formed, in which the blood component collection cassette is configured to be attachable to a blood component separation device having, for load detection, a first load detector and a second load detector, the flow path has a first line through which blood flows when the blood component separation device is in operation and a second line through which blood does not flow when the blood component separation device is in operation, the cassette body includes a first line forming member made of a soft material to form the first line and a second line forming member made of a soft material to form the second line, the first line forming member is provided with a first pressure-receiving portion to be pressed by the first load detector in an attached state in which the blood component collection cassette is attached to the blood component separation device, and the second line forming member is provided with a second pressure-receiving portion to be pressed by the second load detector in the attached state.

When the blood component collection cassette having the above-mentioned configuration is used, it is possible to accurately measure a circuit internal pressure (negative pressure and positive pressure) based on a load detected by the first load detector of the blood component separation device and a load detected by the second load detector. That is, a load obtained by adding an internal pressure of the first line through which blood flows and a reaction force of the first pressure-receiving portion (restoring force caused by deformation of the first pressure-receiving portion) is detected by the first load detector. Meanwhile, a load caused by a reaction force of the second pressure-receiving portion is detected by the second load detector. Therefore, a load caused by the internal pressure of the first line through which blood flows is obtained by subtracting the load detected by the second load detector from the load detected by the first load detector. Further, the circuit internal pressure can be calculated based on the load caused by the internal pressure of the first line. Even though the reaction force of the first pressure-receiving portion decreases over time, since a load caused by the reaction force of the second pressure-receiving portion which similarly decreases is detected in real time and used for calculation of the circuit internal pressure, it is possible to eliminate a measurement error due to a decrease in reaction force over time, and to suppress deterioration of measurement accuracy of the circuit internal pressure. In addition, when compared to a high pressure region, in a low pressure region, a reaction force is relatively large, and thus an influence on the measurement error tends to be large. However, according to the present invention, when a reaction force decreasing over time is detected, it is possible to accurately measure a circuit internal pressure by excluding a measurement error.

It is preferable that the cassette body has a first sheet and a second sheet, which are made of a soft material, the first sheet and the second sheet are overlapped in a thickness direction and coupled to each other, and the flow path is formed between the first sheet and the second sheet.

Since the blood component collection cassette can be manufactured by joining the first sheet and the second sheet made of the soft material, it is possible to perform manufacture at low cost when compared to a conventional cassette made of a hard resin and manufactured by injection molding.

It is preferable that the first pressure-receiving portion and the second pressure-receiving portion are formed in the same shape.

According to this configuration, it is possible to surely eliminate a measurement error.

It is preferable that at least the first pressure-receiving portion and the second pressure-receiving portion form open flow paths in a natural state in which the cassette body is not elastically deformed.

It is preferable that the first line and the second line communicate with each other.

According to this configuration, it is possible to simultaneously form the first line and the second line using blow molding in a process of manufacturing the cassette body.

It is preferable that at least one of the first line forming member and the second line forming member has a standard portion having a relatively small flow path width and a wide portion having a larger flow path width than the flow path width of the standard portion, and the wide portion is included in the first pressure-receiving portion or the second pressure-receiving portion.

According to this configuration, when the blood component collection cassette is attached to the blood component separation device, the first pressure-receiving portion or the second pressure-receiving portion may be surely brought into contact with the first load detector or the second load detector.

The cassette body may have a cassette base portion which supports the first line forming member and the second line forming member and is made of a hard material.

In addition, the present invention is a blood component collection system including a blood component separation device having a first load detector and a second load detector, and a blood component collection cassette configured to be attachable to the blood component separation device, in which the blood component collection cassette includes a cassette body in which a flow path is formed, the flow path has a first line through which blood flows when the blood component separation device is in operation and a second line through which blood does not flow when the blood component separation device is in operation, the cassette body includes a first line forming member made of a soft material to form the first line and a second line forming member made of a soft material to form the second line, the first line forming member is provided with a first pressure-receiving portion to be pressed by the first load detector in an attached state in which the blood component collection cassette is attached to the blood component separation device, the second line forming member is provided with a second pressure-receiving portion to be pressed by the second load detector in the attached state, and the blood component separation device obtains an internal pressure of the first line based on a load detected by the first load detector and a load detected by the second load detector.

In the blood component collection system, it is preferable that the cassette body has a first sheet and a second sheet, which are made of a soft material, the first sheet and the second sheet are overlapped in a thickness direction and coupled to each other, and the flow path is formed between the first sheet and the second sheet.

In the blood component collection system, it is preferable that the first line and the second line communicate with each other, and the blood component separation device includes a clamp allowed to press the cassette body to block the flow path between the first line and the second line.

In the blood component collection system, it is preferable that the first pressure-receiving portion and the second pressure-receiving portion are formed in the same shape.

In the blood component collection system, it is preferable that at least one of the first line forming member and the second line forming member has a standard portion having a relatively small flow path width and a wide portion having a larger flow path width than the flow path width of the standard portion, and the wide portion is included in the first pressure-receiving portion or the second pressure-receiving portion.

According to this configuration, when the blood component collection cassette is attached to the blood component separation device, the first pressure-receiving portion or the second pressure-receiving portion may be surely brought into contact with the first load detector or the second load detector.

In addition, the present invention is a blood component collection kit configured to be attached to a blood component separation device having a first load detector and a second load detector, including a blood collection needle for collecting blood from a donor, and a flow path member in which a flow path is formed to connect the blood collection needle and a centrifugal unit of the blood component separation device to each other, in which the flow path has a first line and a second line branching from the first line, the first line is supplied with the blood collected from the donor, the second line is filled with air, the flow path member has a first line forming member made of a soft material to form the first line and a second line forming member made of a soft material to form the second line, the first line forming member is provided with a first pressure-receiving portion to be pressed by the first load detector in an attached state in which the blood component collection kit is attached to the blood component separation device, and the second line forming member is provided with a second pressure-receiving portion to be pressed by the second load detector in the attached state.

In addition, the present invention is a flow path internal pressure detection method of detecting a pressure in a flow path of a blood component collection cassette attached to a blood component separation device for collecting a blood component, the blood component collection cassette including a cassette body in which a flow path is formed, the flow path having a first line and a second line, the cassette body having a first line forming member made of a soft material to form the first line and a second line forming member made of a soft material to form the second line, the flow path internal pressure detection method including a first measurement step of pressing the first line forming member in a state in which blood is sent to the first line and measuring a load $\alpha 1$ caused by pressing of the first line forming member, a second measurement step of pressing the second line forming member in a state in which blood is not sent to the second line and measuring a load $\alpha 2$ caused by pressing of the second line forming member, a load calculation step of calculating a differential load $\alpha$ obtained by subtracting the load $\alpha 2$ measured in the second measurement step from the load $\alpha 1$ measured in the first measurement step, and an internal pressure calculation step of calculating an internal pressure of the first line based on the calculated differential load $\alpha$.

Advantageous Effects of Invention

According to a blood component collection cassette, a blood component collection kit, a blood component collection system, and a flow path internal pressure detection method of the present invention, it is possible to accurately measure a circuit internal pressure in negative pressure and positive pressure regions using a simple and economical configuration.

DESCRIPTION OF EMBODIMENTS

Hereinafter, a description will be given of a blood component collection cassette, a blood component collection kit, a blood component collection system, and a flow path internal pressure detection method according to the present invention with reference to accompanying drawings using preferred embodiments.

Figure 1:
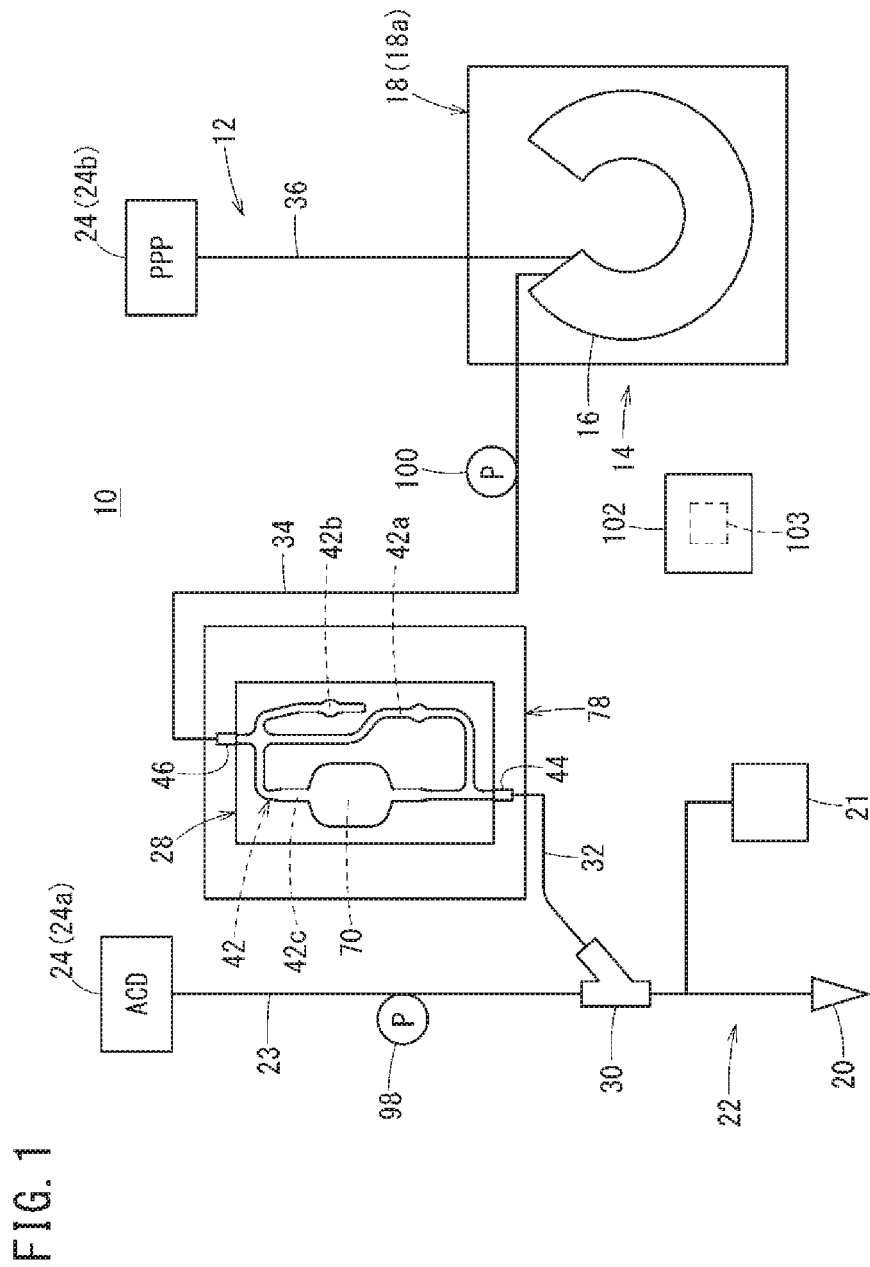
FIG. 1 is a schematic view of a blood component collection system according to an embodiment of the present invention.

In FIG. 1, a blood component collection system 10 is configured as a blood apheresis system that continuously extracts blood (whole blood) from a donor and centrifugally separates the blood outside a body, thereby collecting a specific blood component (plasma (platelet poor plasma: PPP) in the present embodiment) and returns remaining blood components to the donor.

First, a description will be given of an outline of the blood component collection system 10 illustrated in FIG. 1. The blood component collection system 10 includes a blood collection circuit set 12 for storing and flowing a blood component, and a centrifugal separator 14 (blood component separation device) for applying a centrifugal force to the blood collection circuit set 12. The blood collection circuit set 12 has a blood processing unit 16 to which whole blood extracted from the donor is introduced and which centrifugally separates the whole blood into a plurality of blood components. The centrifugal separator 14 includes a centrifugal unit 18 having a rotor 18a for applying a centrifugal force to the blood processing unit 16. The blood processing unit 16 can be attached to the centrifugal unit 18.

The blood collection circuit set 12 is disposed of after being used once for contamination prevention and hygiene. The blood collection circuit set 12 includes a blood collection/blood return portion 22 having a blood collection needle 20 and an initial flow blood collection bag 21, the blood processing unit 16, a plurality of bags 24, and a blood component collection cassette 28 (hereinafter abbreviated to "cassette 28") connected to these elements via tubes. The plurality of bags 24 include an ACD solution bag 24a accommodating an ACD solution corresponding to an anti-coagulant and a PPP bag 24b for storing plasma (platelet poor plasma).

The blood collection/blood return portion 22 is connected to the ACD solution bag 24a and the cassette 28 via a tube connector 30. The ACD solution bag 24a is connected to the tube connector 30 via the ACD solution transfer tube 23.

The cassette 28 is connected to the blood collection/blood return portion 22 via the donor-side tube 32 and is connected to the blood processing unit 16 via a processing unit-side tube 34. The blood processing unit 16 is attached to the centrifugal unit 18 (rotor 18a) of the centrifugal separator 14, and is configured in a container shape so that blood can be introduced, flowed, and flowed out. The PPP bag 24b is connected to the blood processing unit 16 via the PPP transfer tube 36.

Figure 2:
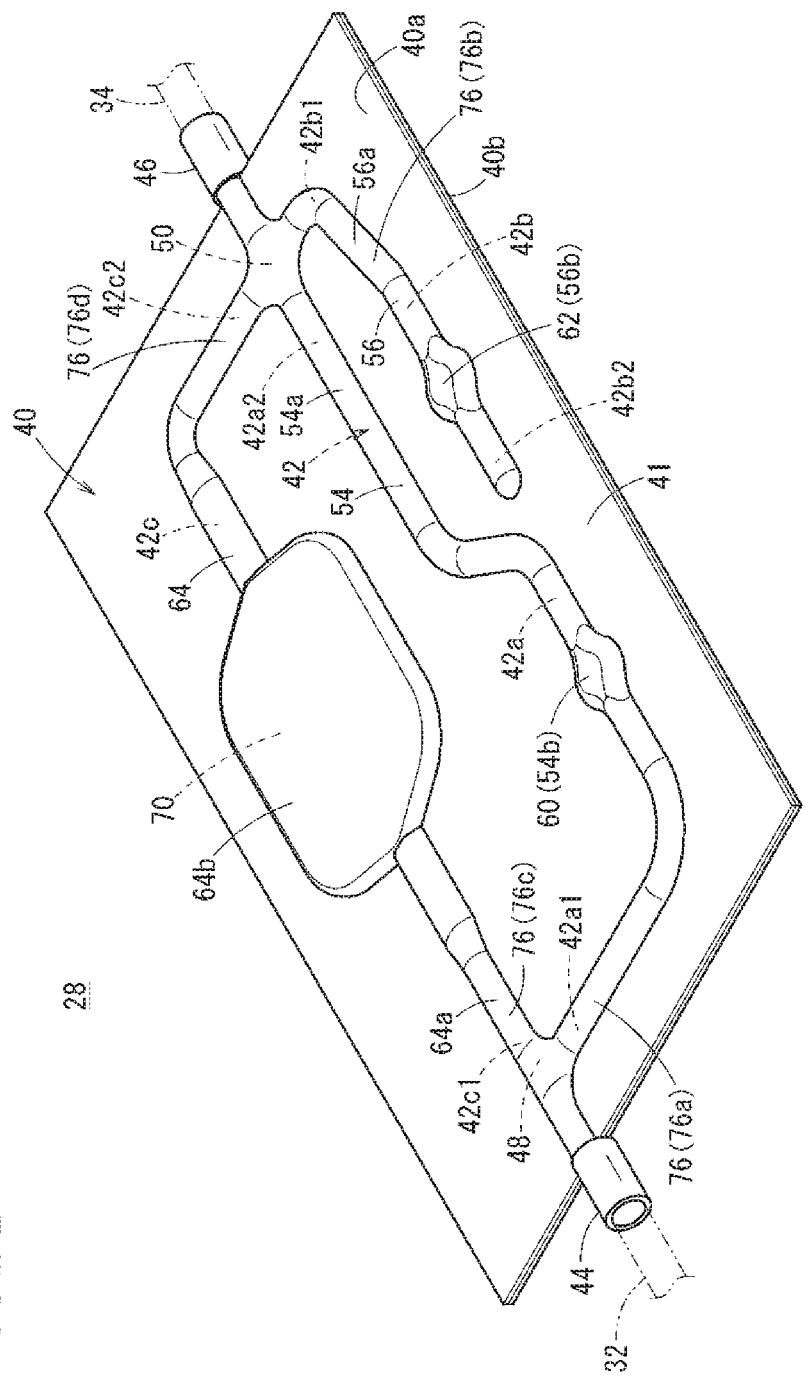
FIG. 2 is a perspective view of a blood component collection cassette.

In FIG. 2, the cassette 28 includes a cassette body 40 in which a flow path 42 is formed. The cassette body 40 is formed in a rectangular shape in plan view. The cassette body 40 has a first sheet 40a and a second sheet 40b made of a soft material. The first sheet 40a and the second sheet 40b are overlapped in a thickness direction and joined to each other.

Examples of the first sheet 40a and the second sheet 40b include vinyl chloride, polyolefin, polyurethane, etc.

The flow path 42 is formed between the first sheet 40a and the second sheet 40b. Examples of joining means between the first sheet 40a and the second sheet 40b include welding (high frequency welding, heat welding, etc.), adhesion, etc. In addition, a first port member 44 and a second port member 46 are provided on a peripheral edge of the cassette body 40. The first port member 44 is connected to one end side of the flow path 42. The second port member 46 is connected to the other end side of the flow path 42. A donor-side tube 32 and a processing unit-side tube 34 are connected to the port members 44 and 46, respectively.

The flow path 42 formed in the cassette body 40 includes a first line 42a through which blood flows during operation of the centrifugal separator 14, a second line 42b through which blood does not flow during operation of the centrifugal separator 14, and a filter line 42c in which a filter member 70 is disposed. One end side 42a1 of the first line 42a and one end side 42c1 of the filter line 42c are connected via a first coupling portion 48. The other end side 42a2 of the first line 42a and the other end side 42c2 of the filter line 42c are connected via a second coupling portion 50.

One end side 42b1 of the second line 42b is connected to the other end side 42a2 of the first line 42a and the other end side 42c2 of the filter line 42c via the second coupling portion 50. The other end side 42b2 of the second line 42b is closed. The first line 42a, the second line 42b and the filter line 42c at least partially extend in parallel. At least a part of the first line 42a extends between the second line 42b and the filter line 42c extending in parallel. Each of the first coupling portion 48 and the second coupling portion 50 is included in a part of the flow path 42.

A wall portion of the cassette body 40 forming the flow path 42 convexly bulges in the thickness direction of the cassette 28 on both surface sides of the cassette body 40 even when no positive pressure acts in the flow path 42. Therefore, the flow path 42 is a flow path which is open in a natural state. The flow path 42 at a pressed position is elastically deformable in a closing direction at the time of being pressed by an external force.

The cassette body 40 has a first line forming member 54 forming the first line 42a and a second line forming member 56 forming the second line 42b. A first pressure-receiving portion 60 pressed by a first load detector 88 (described below), which is mounted on the centrifugal separator 14 in a cassette attached state in which the cassette 28 is attached to the centrifugal separator 14, is provided in the first line forming member 54. A second pressure-receiving portion 62 pressed by a second load detector 90 (described below) mounted on the centrifugal separator 14 in the cassette attached state is provided in the second line forming member 56.

Each of the first pressure-receiving portion 60 and the second pressure-receiving portion 62 is included in a part of the flow path 42. Therefore, the first pressure-receiving portion 60 and the second pressure-receiving portion 62 bulge from the sheet surface 41 (base surface) of the cassette body 40 in the thickness direction of the cassette body 40. The first pressure-receiving portion 60 and the second pressure-receiving portion 62 are formed to have the same shape and same size. Therefore, the first pressure-receiving portion 60 and the second pressure-receiving portion 62 have the same rigidity.

The first line forming member 54 has a standard portion 54a having a relatively small flow path width and a wide portion 54b having a larger flow path width than that of the standard portion 54a. The wide portion 54b is included in the first pressure-receiving portion 60. The second line forming member 56 has a standard portion 56a having a relatively small flow path and a wide portion 56b having a larger flow path width than that of the standard portion 56a. The wide portion 56b is included in the second pressure-receiving portion 62. In the first line forming member 54 or the second line forming member 56, the wide portion 54b or the wide portion 56b may not be provided.

The cassette body 40 has a filter line forming member 64 forming the filter line 42c. The filter line forming member 64 has a standard portion 64a and a filter accommodating portion 64b which is wider than the standard portion 64a. A filter member 70 for removing a substance in which blood components are aggregated (hereinafter referred to as a "blood clump") is accommodated in the filter accommodating portion 64b.

A plurality of clamping action portions 76 (76a to 76d), on which a plurality of clamps 72 (72a to 72d) (see FIG. 3) provided in the centrifugal separator 14 acts, is provided in the cassette 28. When the cassette 28 is mounted on the centrifugal separator 14, the clamping action portions 76 but on or face the corresponding clamps 72. Specifically, the clamping action portions 76 are provided at a position forming an end of the first line 42a on a side of the first port member 44, a position close to the second coupling portion 50 of the second line 42b, and positions forming both ends of the filter line 42c, in the cassette 28.

A flow path configuration formed in the cassette 28 and the number and arrangement of the bags to be provided are not limited to the configuration described above and illustrated and may be altered according to a type of blood component to be collected, a usage method, etc.

A method of manufacturing the cassette 28 having the above-described configuration includes a molding process of superposing the first sheet 40a and the second sheet 40b, welding the first sheet 40a and the second sheet 40b to form the flow path 42 between the first sheet 40a and the second sheet 40b, thereby molding the cassette 28 having the cassette body 40, and a sterilization step of sterilizing the cassette 28 obtained by the molding process.

In the molding process, for example, sheet-like materials are drawn from two material rolls obtained by winding the sheet-like materials corresponding to materials of the first sheet 40a and the second sheet 40b around the two material rolls, respectively, and supplied to a joining device such as a high frequency welding device together with assembled parts (the filter member 70 and the port members 44 and 46). The joining device has upper and lower molds, and blow molding is performed while joining the two sheet-like materials together with the assembled parts to mode the cassette 28 in which the flow path 42 is formed. In this case, the tubes 32 and 34 may be connected at the time of molding the cassette 28 using the joining device.

In the sterilization process, for example, autoclave sterilization is performed on the cassette 28 obtained by the molding process. The cassette 28 is made of a material which can withstand heat of autoclave sterilization, and thus is not melted by heat during sterilization. In addition, since the cassette 28 is made of a material having water vapor permeability, water vapor, which is a processing gas for autoclave sterilization, is introduced into the flow path 42 of the cassette 28. Therefore, the cassette 28 can be suitably sterilized. In the sterilization process, EOG sterilization may be performed.

In a sterilization process, the whole blood collection circuit set 12 including the plurality of bags 24 (ACD solution bag 24a, etc.) may be sterilized. In this way, the blood collection circuit set 12 can be efficiently sterilized.

In FIG. 1, the centrifugal separator 14 is a device repeatedly used in blood component collection, and is provided, for example, in a medical facility, a blood collecting vehicle, etc. The centrifugal separator 14 includes the centrifugal unit 18 having the rotor 18a and the cassette attaching portion 78 configured to allow the cassette 28 of the blood collection circuit set 12 to be attached thereto.

Figure 3:
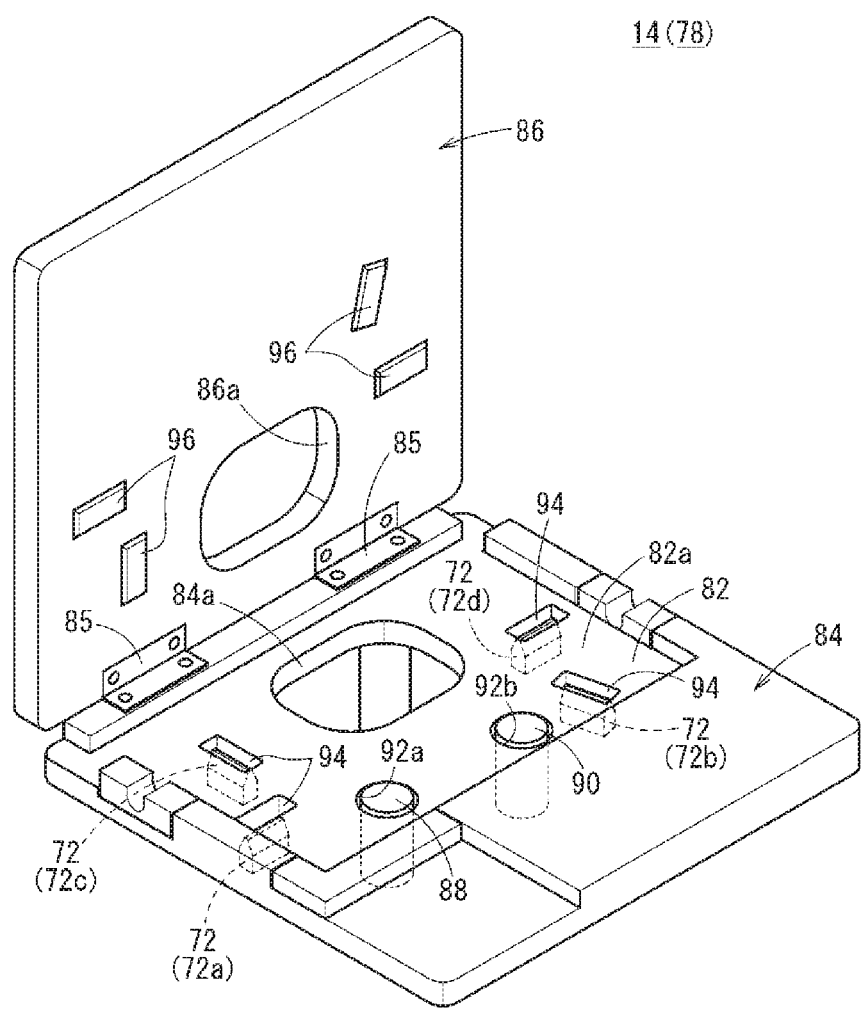
FIG. 3 is a perspective view of a cassette attaching portion.

As illustrated in FIG. 3, the cassette attaching portion 78 includes an attachment base 84 having a cassette mounting groove 82 formed therein, an openable and closable lid body 86 configured to cover the attachment base 84 when closed, a first load detector 88 capable of pressing the first pressure-receiving portion 60 of the cassette 28 (see FIG. 2), a second load detector 90 capable of pressing the second pressure-receiving portion 62 (see FIG. 2) of the cassette 28, and the plurality of clamps 72 configured to be capable of pressing the clamping action portion 76 of the cassette 28.

The lid body 86 is rotatably connected to the attachment base 84 via a hinge 85. When the lid body 86 is closed in a state in which the cassette 28 is held in the cassette mounting groove 82 of the attachment base 84, the cassette 28 is interposed between the attachment base 84 and the lid body 86. Openings 84a and 86a capable of accommodating the filter accommodating portion 64b of the cassette 28 are provided in the attachment base 84 and the lid body 86, respectively. In this way, the filter accommodating portion 64b is prevented from being crushed while properly holding the cassette 28 between the attachment base 84 and the lid body 86.

The first load detector 88 is inserted into a first through-hole 92a provided in the attachment base 84 and exposed in the cassette mounting groove 82. An upper surface of the first load detector 88 protrudes from a bottom surface 82a of the cassette mounting groove 82. The second load detector 90 is inserted into a second through-hole 92b provided in the attachment base 84 and exposed in the cassette mounting groove 82. An upper surface of the second load detector 90 protrudes from the bottom surface 82a of the cassette mounting groove 82. A protrusion height of the first load detector 88 from the bottom surface 82a is the same as a protrusion height of the second load detector 90 from the bottom surface 82a. For example, the first load detector 88 and the second load detector 90 include load cells.

The plurality of clamps 72 (72a to 72d) can advance and retreat in the thickness direction of the cassette 28 in a state held in the cassette mounting groove 82, and are disposed to correspond to arrangement of the plurality of clamping action portions 76 (76a to 76d) provided in the cassette 28. The plurality of clamps 72 can press the plurality of clamping action portions 76, respectively, via a plurality of holes 94 opening to the bottom surface 82a of the cassette mounting groove 82. In the lid body 86, a plurality of projections 96 is provided at positions corresponding to the plurality of holes 94 (clamps 72) when closed.

When the clamping action portion 76 is not pressed by the clamp 72 in a state in which the cassette 28 is attached to the cassette attaching portion 78, the flow path in the clamping action portion 76 is open. When the clamp 72 protrudes from the hole 94 and presses the clamping action portion 76, the flow path in the clamping action portion 76 is blocked. Further, when the clamp 72 moves backward, due to an elastic restoring force of the cassette body 40 (clamping action portion 76), the clamping action portion 76 returns to an original shape and the flow path in the clamping action portion 76 opens.

As illustrated in FIG. 1, the centrifugal separator 14 includes an ACD solution transfer pump 98 acting on the ACD solution transfer tube 23 and a blood collection/blood return pump 100 acting on the processing unit-side tube 34 connected to the cassette 28. The ACD solution transfer pump 98 is a pump that transfers the ACD solution from the ACD solution bag 24a to the cassette 28 and the blood processing unit 16 via the ACD solution transfer tube 23. The blood collection/blood return pump 100 is a pump that transfers blood from the donor side to the blood processing unit 16 and transfers blood from the blood processing unit 16 to the donor. For example, the ACD solution transfer pump 98 and the blood collection/blood return pump 100 include a roller pump and a finger pump.

The centrifugal separator 14 further includes a controller 102 that controls the centrifugal unit 18, the cassette attaching portion 78, and the pumps 98 and 100. Operations of the plurality of clamps 72 are controlled by the controller 102. The controller 102 has an arithmetic unit 103 that obtains (calculates) a circuit internal pressure of the blood collection circuit set 12 based on a load detected by the first load detector 88 and the second load detector 90 (FIG. 3) when the centrifugal separator 14 is in operation.

Next, a description will be given of an operation of the blood component collection system 10 according to the present embodiment configured as described above in relation to the flow path internal pressure detection method according to the present embodiment.

As a preparation (set-up) for collecting a blood component from the donor using the blood component collection system 10 illustrated in FIG. 1, the blood collection circuit set 12 is attached to the centrifugal separator 14.

Specifically, the cassette 28 is attached to the cassette attaching portion 78, and the blood processing unit 16 is attached to the rotor 18a. On the other hand, the blood collection needle 20 pierces the donor.

Figure 4:
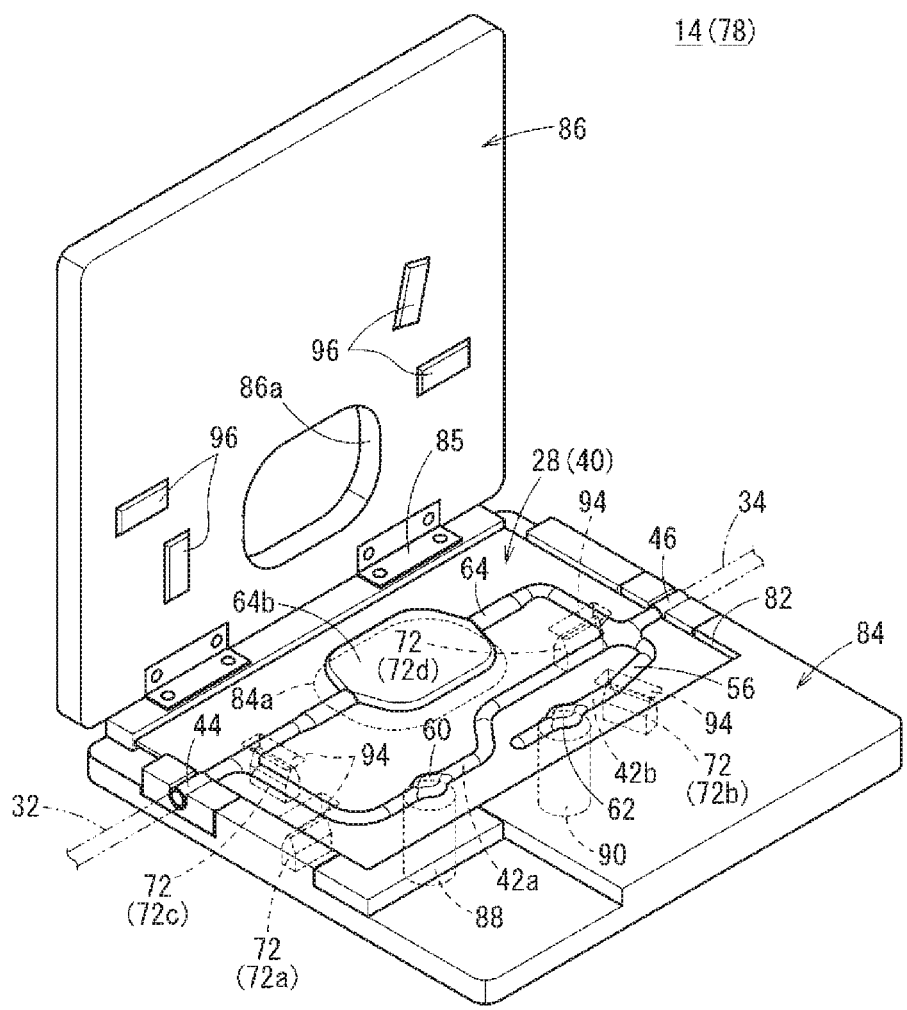
FIG. 4 is a perspective view of the cassette attaching portion in a state in which the blood component collection cassette is placed.

When the cassette 28 is attached to the cassette attaching portion 78, as illustrated in FIG. 4, the cassette 28 is first mounted in the cassette mounting groove 82. Further, when the lid body 86 is closed, the cassette 28 is held between the attachment base 84 and the lid body 86. As a result, the first pressure-receiving portion 60 and the second pressure-receiving portion 62 of the cassette 28 are pressed by the first load detector 88 and the second load detector 90, and are in a state of being slightly elastically deformed. In this case, the amount of deformation of the first pressure-receiving portion 60 due to being pressed by the first load detector 88 is the same as the amount of deformation of the second pressure-receiving portion 62 due to being pressed by the second load detector 90. In addition, the plurality of clamping action portions 76 of the cassette 28 is placed opposite to the plurality of clamps 72.

When the centrifugal separator 14 illustrated in FIG. 1 is instructed to start an operation by an operation of the user, priming using the ACD solution is executed under action of the ACD solution transfer pump 98 in the centrifugal separator 14. Specifically, the ACD solution is introduced from the ACD solution bag 24a to the flow path 42 in the cassette 28 via the ACD solution transfer tube 23, and the priming using the ACD solution is terminated in a stage in which it is detected by a line sensor (not illustrated) disposed on the flow path 42 (or outside the cassette 28) that the ACD solution has reached the vicinity of the filter line 42c.

Subsequently, the centrifugal separator 14 applies a centrifugal force to the blood processing unit 16 attached to the rotor 18a by rotating the rotor 18a, and operates the blood collection/blood return pump 100 to extract blood (whole blood) from the donor and introduce blood into the blood processing unit 16 (blood collection operation). The blood introduced into the blood processing unit 16 is separated into red blood cells (concentrated red blood cells), buffy coat and plasma (platelet poor plasma) by a centrifugal force accompanying rotation of the rotor 18a.

The plasma separated in the blood processing unit 16 is introduced into the PPP bag 24b via a PPP transfer tube 36. The remaining blood components (erythrocytes and buffy coat) are returned to the donor after centrifugation (blood return operation). In this instance, blood clumps contained in the remaining blood components is trapped by the filter member 70 provided on the filter line 42c of the cassette 28, and thus it is possible to reduce a risk of blood clumps returning to the donor. The blood collection operation and the blood return operation described above are repeated a plurality of times.

When the blood component collection system 10 is in operation, the clamp 72 (FIG. 3) of the centrifugal separator 14 operates as follows.

Figure 5:
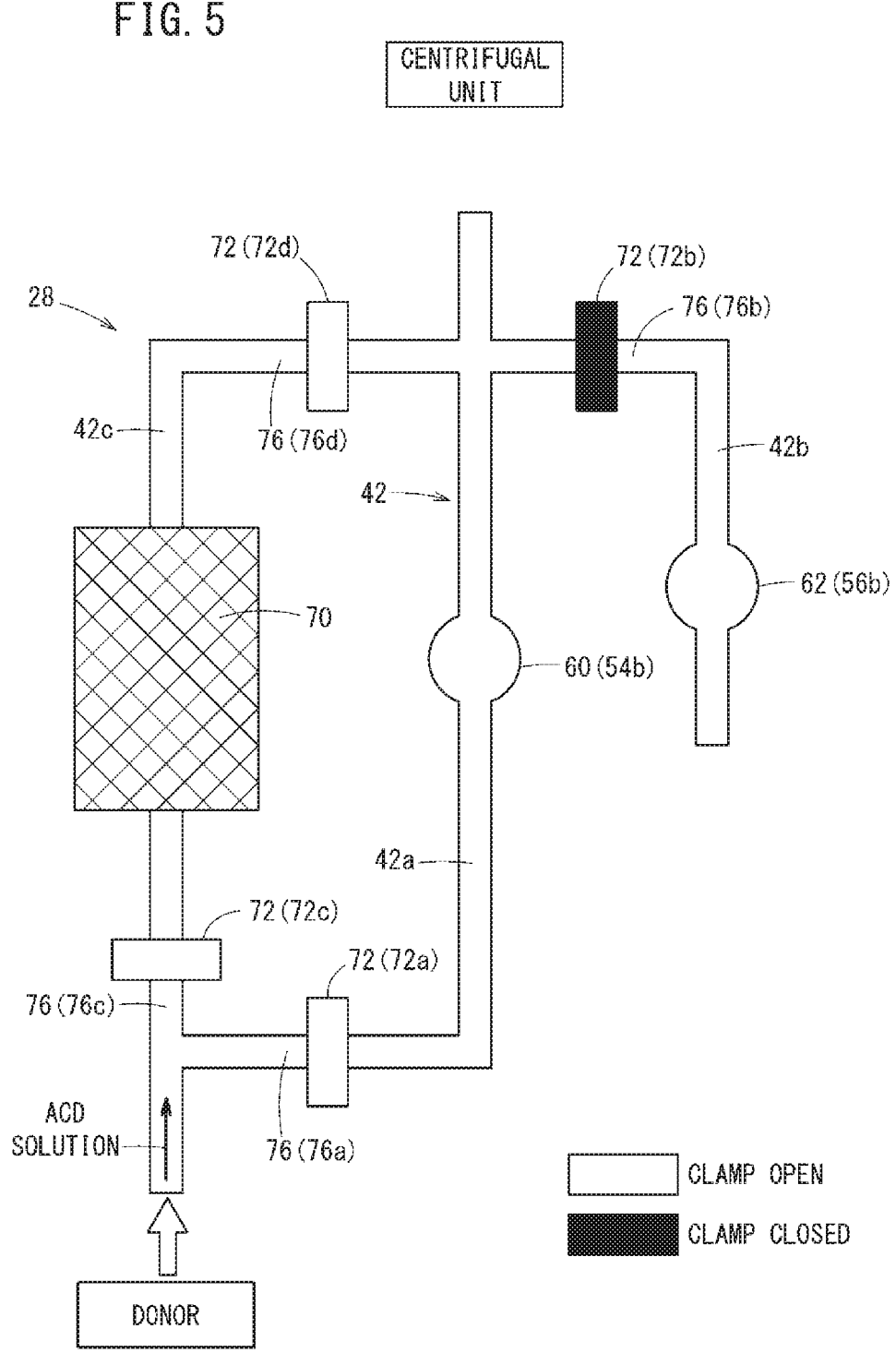
FIG. 5 is a first explanatory diagram for description of an operation of a clamp.

As illustrated in FIG. 5, when priming is performed using the ACD solution, the clamp 72b is closed, and the clamps 72a, 72c, and 72d are opened. In this way, the second line 42b is cut off from the other flow path 42. In addition, in this state, the ACD solution is introduced into the flow path 42 nearest to the first line 42a of the cassette 28, and the priming using the ACD solution is terminated in a stage in which it is detected by a line sensor (not illustrated) on the flow path 42 (or outside the cassette 28) that the ACD solution has reached the vicinity of the first line 42a.

Figure 6:
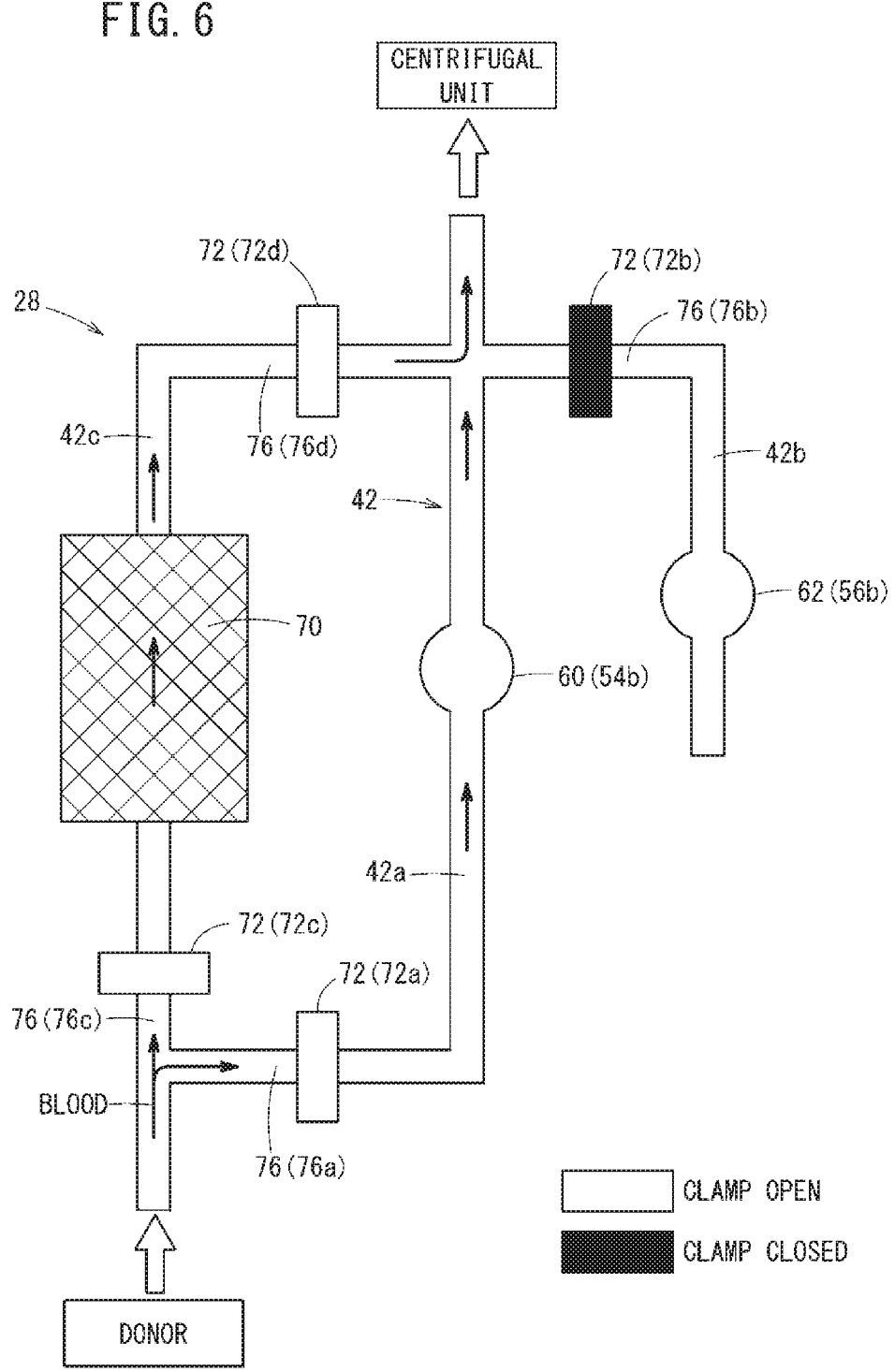
FIG. 6 is a second explanatory diagram for description of an operation of the clamp.

Subsequently, at the time of performing first blood collection, as illustrated in FIG. 6, a state in which the clamp 72b is closed and the clamps 72a, 72c, and 72d are open is maintained. Then, in this state, blood from the donor is introduced into the flow path 42 other than the second line 42b of the cassette 28, and all air in a circuit of the cassette 28 is pushed out to the blood processing unit 16 by the blood.

Figure 7:
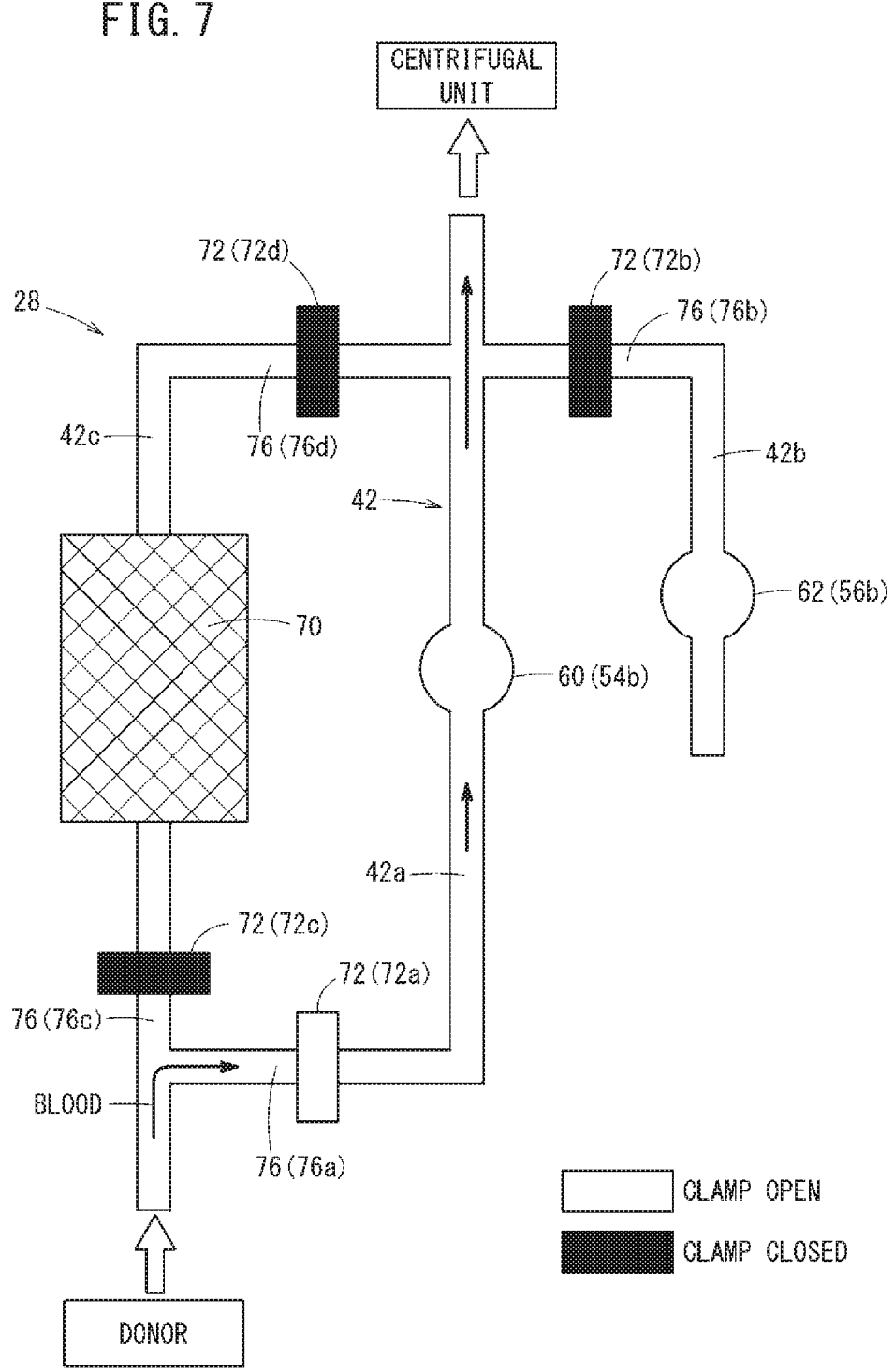
FIG. 7 is a third explanatory diagram for description of an operation of the clamp.

During the first blood collection, as illustrated in FIG. 7, the filter line 42c is closed by closing the clamps 72c and 72d, which prevents negative pressure from acting on the filter accommodating portion 64b and blocking the filter accommodating portion 64b.

Figure 8:
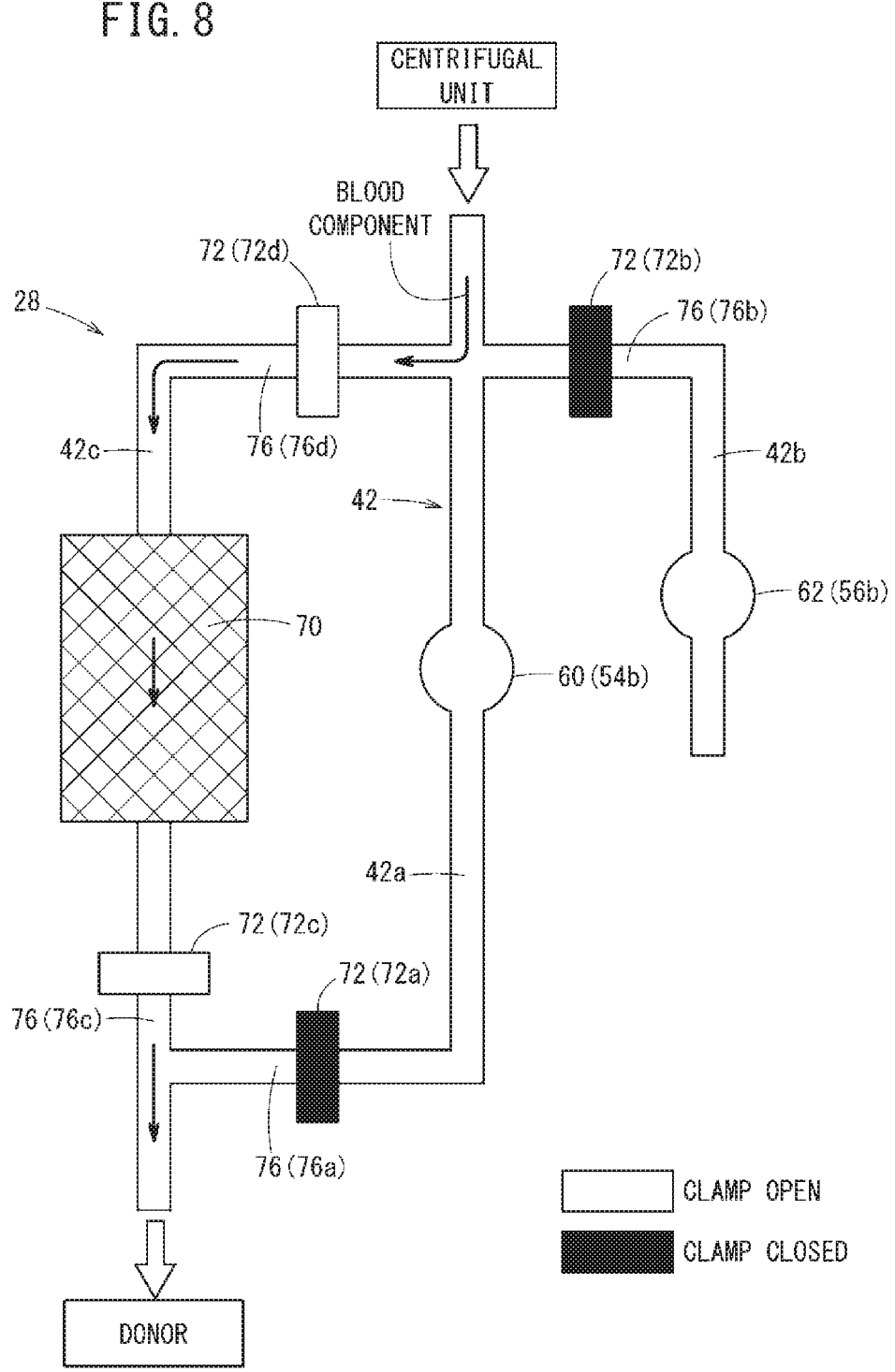
FIG. 8 is a fourth explanatory diagram for description of an operation of the clamp.

Subsequently, when a blood component is returned to the donor, as illustrated in FIG. 8, the clamp 72a is closed and the clamps 72c and 72d are opened, thereby closing the first line 42a and opening the filter line 42c. Therefore, when a blood component passes through the filter member 70, a blood clump contained in the blood component is trapped in the filter member 70. Since the first line 42a is closed, blood clumps do not returned to the donor via the first line 42a.

Figure 9:
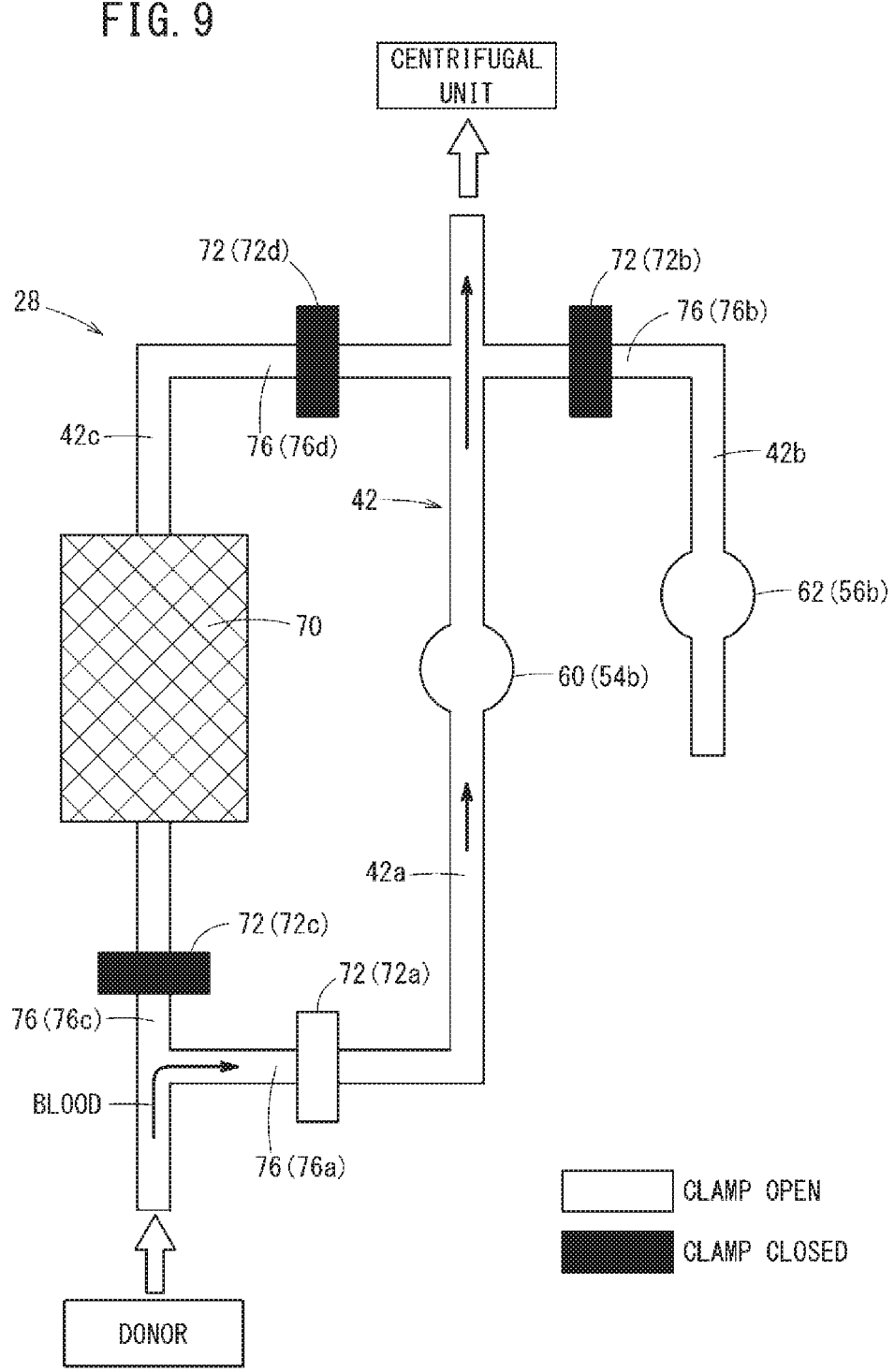
FIG. 9 is a fifth explanatory diagram for description of an operation of the clamp.

Subsequently, when blood collection is performed for the second time and thereafter, as illustrated in FIG. 9, the clamps 72c and 72d are closed and the clamp 72a is opened, thereby closing the filter line 42c and opening the first line 42a. Accordingly, blood is transferred to the blood processing unit 16 side (the centrifugal unit 18 side) via only the first line 42a in the first line 42a and the filter line 42c. Thereafter, blood return (FIG. 8) is performed again. Such blood collection and blood return are repeated a plurality of times.

Further, at the time of finally returning blood, as illustrated in FIG. 8, the clamp 72a is closed and the clamps 72c and 72d are opened to return blood components to the donor as much as possible.

A flow path internal pressure detection method includes a first measurement step, a second measurement step, a load calculation step, and an internal pressure calculation step. In the first measurement step, the first line forming member 54 in a state in which blood is being sent to the first line 42a is pressed, and a load $\alpha 1$ caused by pressing of the first line forming member 54 is measured.

Specifically, a load received from the first pressure-receiving portion 60 is detected by the first load detector 88. In the second measurement step, the second line forming member 56 in a state in which no blood is being sent to the second line 42b is pressed, and a load $\alpha 2$ caused by pressing of the second line forming member 56 is measured. Specifically, a load received from the second pressure-receiving portion 62 is detected by the second load detector 90.

In the load calculation step, a differential load $\alpha$ obtained by subtracting the load $\alpha 2$ measured in the second measurement step from the load $\alpha 1$ measured in the first measurement step is calculated. In the internal pressure calculation step, an internal pressure of the first line 42a is calculated based on the calculated differential load $\alpha$. In practice, a reaction force based on an elastic restoring force of the first pressure-receiving portion 60 may not be completely equal to a reaction force based on an elastic restoring force of the second pressure-receiving portion 62. For this reason, before calculating the differential load $\alpha$, a step of adjusting $\alpha 1$ and $\alpha 2$ to be equal to each other is performed under the same condition (in a state in which no blood is sent to either the first line 42a or the second line 42b). More specifically, a correction coefficient A for equalization is calculated, and a correction step for establishing $\alpha 1$=correction coefficient A×$\alpha 2$ is performed. Thereafter, the differential load $\alpha$ is calculated.

In this case, the cassette 28, the blood component collection system 10, and the flow path internal pressure detection method according to the present embodiment provide the following effects.

Examples of the sterilization process at the time of manufacturing the cassette 28 illustrated in FIG. 2, etc. include EOG sterilization, autoclave sterilization, etc. In addition, since the cassette body 40 is obtained by welding the first sheet 40a and the second sheet 40b made of a soft material, manufacture may be performed at low cost when compared to a conventional cassette made of a hard resin and manufactured by injection molding.

According to the blood component collection system 10, it is possible to accurately measure the circuit internal pressure (negative pressure and positive pressure) based on the load detected by the first load detector 88 (FIG. 4) of the centrifugal separator 14 and the load detected by the second load detector 90 (FIG. 4) of the centrifugal separator 14. The circuit internal pressure is calculated by the arithmetic unit 103 (FIG. 1) of the centrifugal separator 14. For example, the internal circuit pressure to be measured is in a range of −300 to 500 mmHg.

Figure 10A:
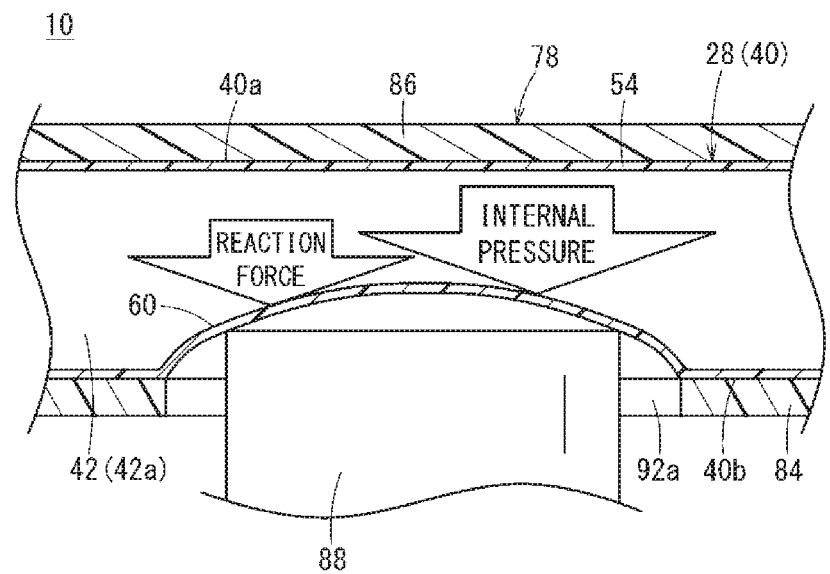
FIG. 10A is a diagram for description of load detection at the time of a positive pressure.
Figure 10B:
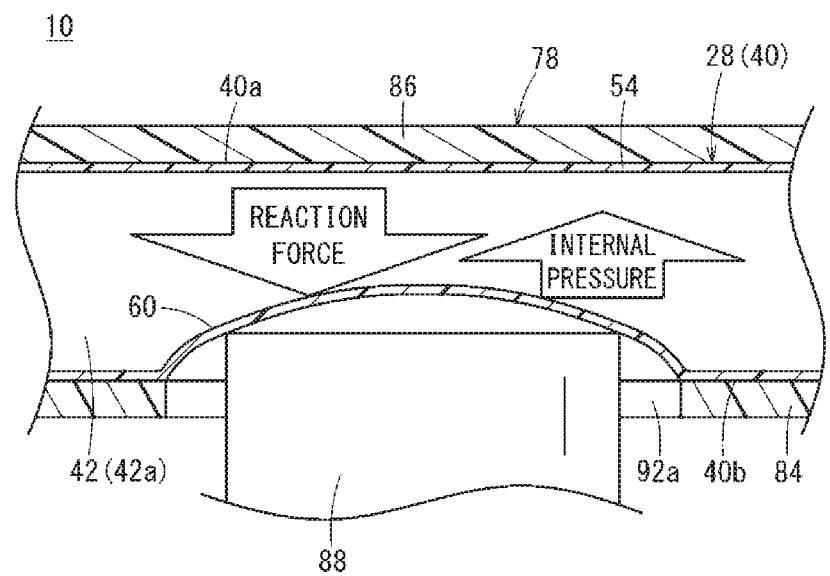
FIG. 10B is a diagram for description of load detection at the time of a negative pressure.

Specifically, a load obtained by adding an internal pressure (circuit internal pressure) of the first line 42a through which blood flows and a reaction force of the first pressure-receiving portion 60 (restoring force due to deformation of the first pressure-receiving portion 60) is detected by the first load detector 88. That is, when the circuit internal pressure is positive, as illustrated in FIG. 10A, a load (pressing force from the first pressure-receiving portion 60) acting on the first load detector 88 is calculated by simply adding the circuit internal pressure and reaction force. On the other hand, when the circuit internal pressure is negative, as illustrated in FIG. 10B, the load acting on the first load detector 88 is obtained by subtracting an absolute value of the circuit internal pressure from the reaction force.

In the blood component collection system 10, a load due to a reaction force of the second pressure-receiving portion 62 is detected by the second load detector 90. To block the second line 42b in a state of a normal pressure, an internal pressure of the second line 42b corresponds to 0 mmHg at all times. For this reason, the load detected by the second load detector 90 only corresponds to the reaction force of the second pressure-receiving portion 62 (restoring force due to deformation of the second pressure-receiving portion 62). Then, a reaction force of the second pressure-receiving portion 62 acting on the second load detector 90 is the same as a reaction force of the first pressure-receiving portion 60 acting on the first load detector 88. Therefore, when the load detected by the second load detector 90 is subtracted from the load detected by the first load detector 88, a load due to the internal pressure of the first line 42a through which blood flows is obtained. Therefore, it is possible to calculate the circuit internal pressure based on the load due to the internal pressure of the first line 42a. In this case, the controller 102 of the centrifugal separator 14 stores a calibration curve (calibration curve data) showing a relationship between a load and a circuit internal pressure, and can calculate a circuit internal pressure using an obtained load and the calibration curve data.

Figure 11:
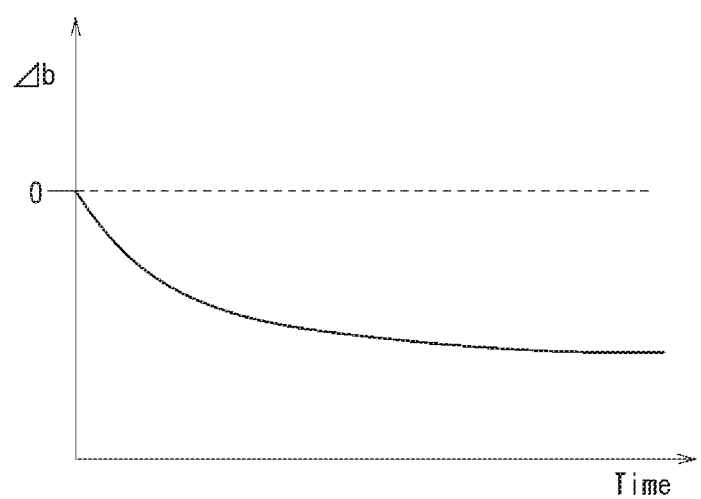
FIG. 11 is a diagram for description of a decrease in reaction force over time.

As illustrated in FIG. 11, the reaction force of the first pressure-receiving portion 60 decreases over time. FIG. 11 illustrates an image of a time change (Δb) of the reaction force of the first pressure-receiving portion 60 when an initial reaction force is set to 0. The reaction force of the first pressure-receiving portion 60 decreases over time as described above since creep occurs as a state in which the first pressure-receiving portion 60 is pressed by the first load detector 88 continues. Therefore, when a fixed value that does not change over time is used as the reaction force of the first pressure-receiving portion 60, measurement accuracy of the circuit internal pressure decreases.

Therefore, in the blood component collection system 10, similarly to the reaction force of the first pressure-receiving portion 60, a load due to the reaction force of the second pressure-receiving portion 62 decreasing over time is detected in real time and used for calculation of the circuit internal pressure. In this way, it is possible to eliminate a measurement error due to the decrease in reaction force over time, and to suppress a decrease in measurement accuracy of the circuit internal pressure. In other words, since the reaction force of the first pressure-receiving portion 60 corresponds to an intercept of a function representing the above-described calibration curve, in the present invention, it is possible to eliminate the measurement error due to the decrease of the reaction force over time by correcting the intercept of the calibration curve in real time using the load detected by the second load detector 90 (reaction force of the second pressure-receiving portion 62).

When compared to a high pressure region, in a low pressure region, a reaction force is relatively large, and thus an influence on the measurement error tends to be large. On the other hand, according to the present invention, it is possible to accurately measure the circuit internal pressure by detecting the reaction force that changes over time in real time to use the detected reaction force, thereby eliminating the measurement error.

In addition, in the cassette 28, the first line 42a and the second line 42b communicate with each other in a natural state in which the cassette body 40 is not elastically deformed. Further, the centrifugal separator 14 includes the clamp 72b capable of pressing the cassette body 40 to close the flow path 42 between the first line 42a and the second line 42b. According to this configuration, in a manufacturing process of the cassette body 40, the first line 42a and the second line 42b can be simultaneously formed by blow molding. In addition, when the centrifugal separator 14 is in operation, it is possible to reliably and easily prevent blood from flowing to the second line 42b by pressing a predetermined position of the cassette body 40 using the clamp 72b.

Further, as illustrated in FIG. 2, at least one of the first line forming member 54 and the second line forming member 56 has a standard portion (the standard portion 54a or 56a) having a relatively small flow path width and a wide portion (the wide portion 54b or 56b) having a larger flow path width than that of the standard portion, and the wide portion is included in the first pressure-receiving portion 60 or the second pressure-receiving portion 62. According to this configuration, when the blood component collection cassette 28 is attached to the centrifugal separator 14, the first pressure-receiving portion 60 or the second pressure-receiving portion 62 may be surely brought into contact with the first load detector 88 or the second load detector 90.

In the above-described cassette 28, the flow path 42 is formed between the first sheet 40a and the second sheet 40b made of a soft material. However, a structure for forming the flow path 42 is not limited to such a configuration. For example, a member of the cassette body forming the flow path 42 may correspond to a tube. In this case, the cassette body includes a first tube (first line forming member) having a flow path included in the first line 42a, a second tube (second line forming member) having a flow path included in the second line 42b, and a third tube included in the filter line 42c, and includes a plate-like cassette base for supporting the first tube, the second tube, and the third tube.

The first pressure-receiving portion 60 and the clamping action portion 76a are provided in the first tube. The second pressure-receiving portion 62 and the clamping action portion 76b are provided in the second tube. The clamping action portions 76c and 76d are provided in the third tube. The cassette base is formed such that the first pressure-receiving portion 60 and the second pressure-receiving portion 62 are exposed, so that the first load detector 88 can press the first pressure-receiving portion 60 and the second load detector 90 can press the second pressure-receiving portion 62. In addition, the cassette base is formed such that the clamping action portions 76a to 76d are exposed, so that the clamps 72a to 72d (FIG. 3) can press the clamping action portions 76a to 76d.

Figure 12:
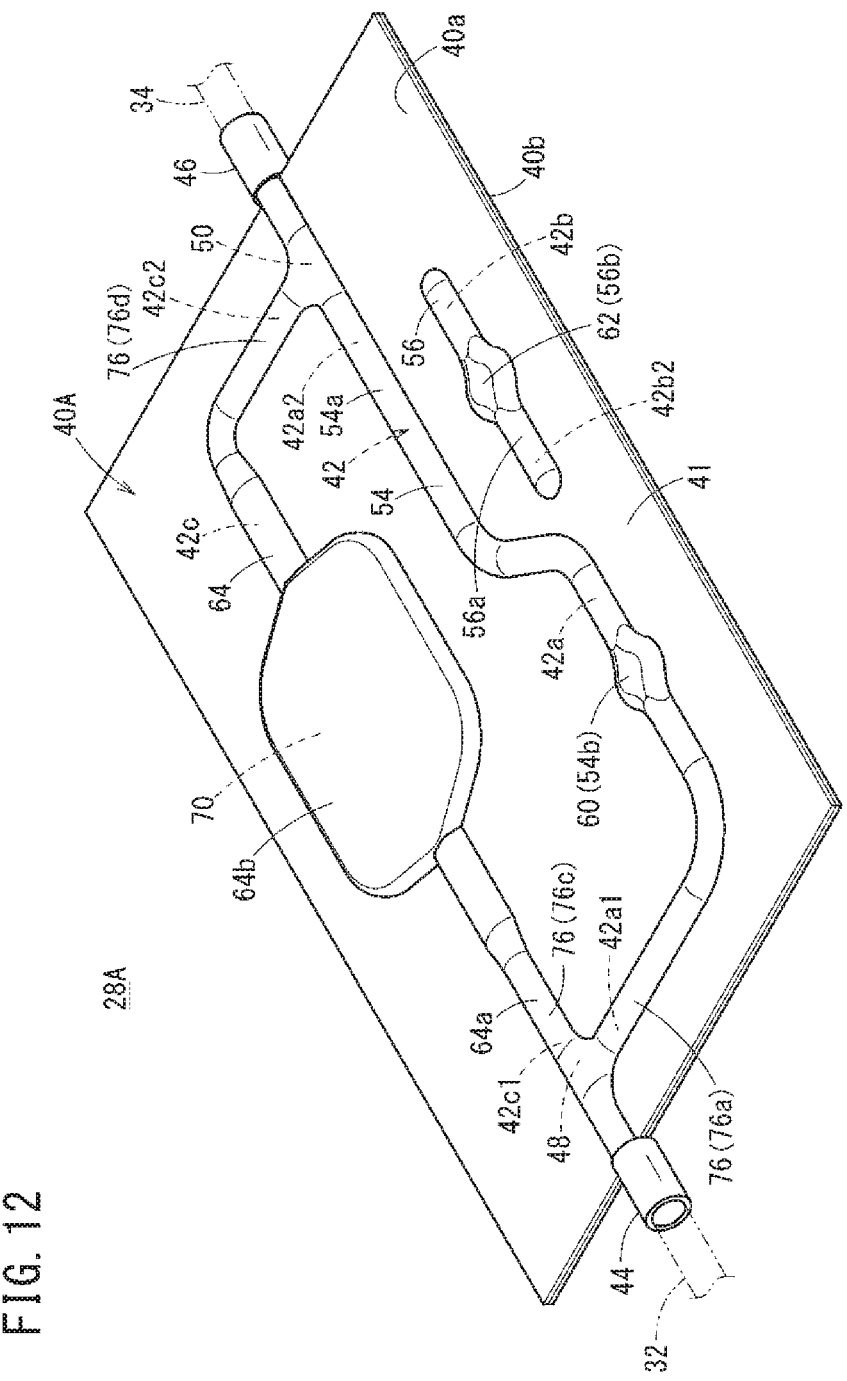
FIG. 12 is a perspective view of a blood component collection cassette according to another embodiment.

In the blood component collection system 10 described above, a blood component collection cassette 28A (hereinafter abbreviated to a "cassette 28A") illustrated in FIG. 12 may be adopted instead of the cassette 28. In a cassette body 40A of the cassette 28A, the second line 42b is a fluid non-communicating flow path independent of the first line 42a. Therefore, the second line 42b corresponds to a space independent of the first line 42a at all times, and air is enclosed in the second line 42b. A configuration of the other part of the cassette 28A is the same as a configuration of the cassette 28 illustrated in FIG. 2, etc. According to the blood component collection cassette 28A, the clamp 72b (FIG. 3) in the centrifugal separator 14 may not be used. Therefore, it is possible to simplify the configuration of the centrifugal separator 14, and to simplify control related to the operation of the clamp 72.

Figure 13:
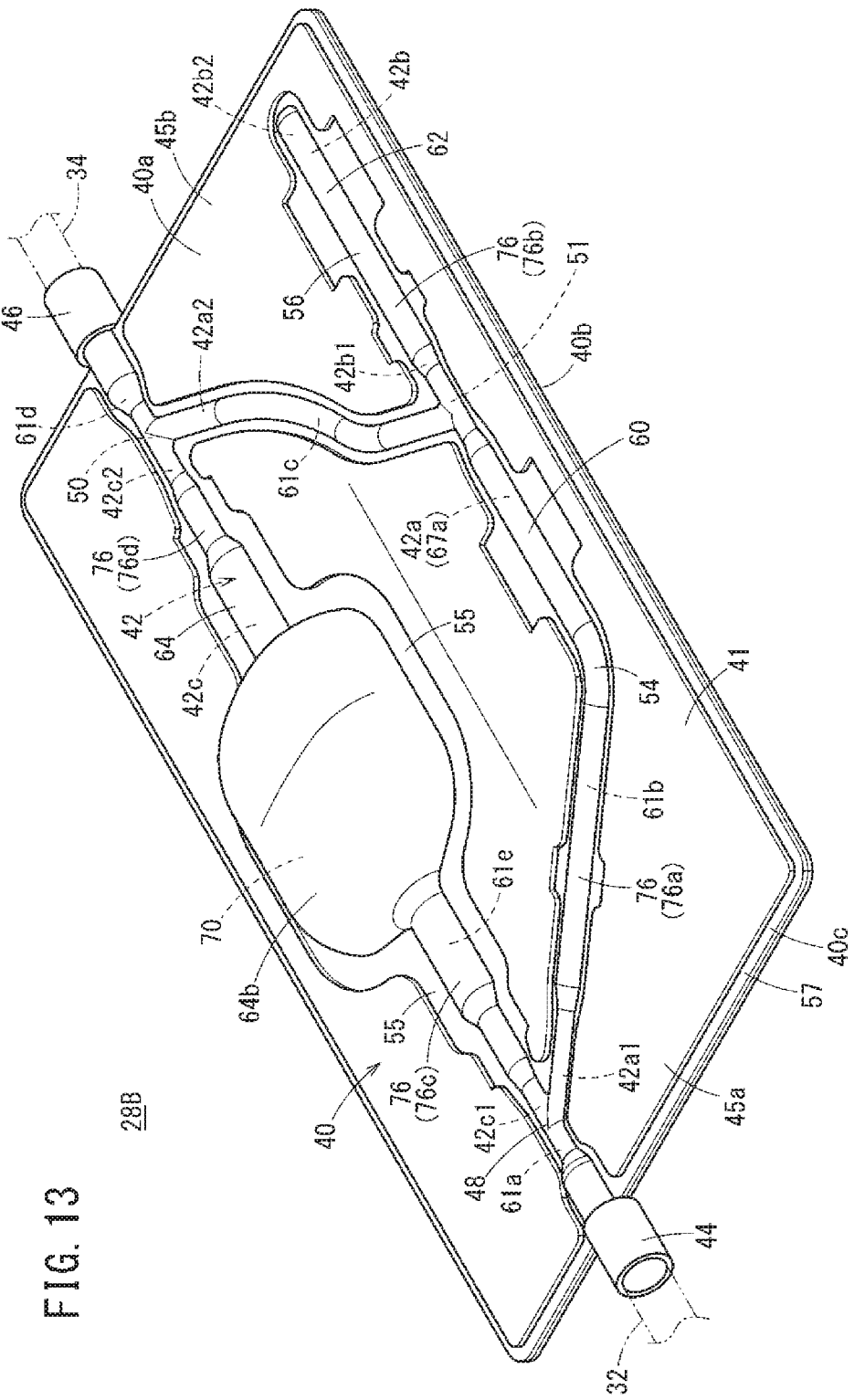
FIG. 13 is a perspective view of a blood component collection cassette according to still another embodiment.

In the blood component collection system 10 described above, a blood component collection cassette 28B (abbreviated to "cassette 28B") illustrated in FIG. 13 may be adopted instead of the cassette 28. The flow path 42 formed in the cassette body 40 of the cassette 28B has a first line 42a through which blood flows when the centrifugal separator 14 is in operation, a second line 42b through which blood does not flow when the centrifugal separator 14 is in operation, and a filter line 42c in which the filter member 70 is disposed.

The rectangular cassette body 40 has a first end 45a which is one end in a major axis direction and a second end 45b which is the other end in the major axis direction. The first port member 44 is provided at the first end 45a. The second port member 46 is provided at the second end 45b. The first port member 44 and the second port member 46 are disposed on the same straight line along a longitudinal axis of the cassette body 40.

The one end side 42a1 of the first line 42a and the one end side 42c1 of the filter line 42c are connected via the first coupling portion 48. The other end side 42a2 of the first line 42a and the other end side 42c2 of the filter line 42c are connected via the second coupling portion 50.

The one end side 42b1 of the second line 42b is connected to an intermediate portion of the first line 42a via a third coupling portion 51. The other end side 42b2 of the second line 42b is closed. The first line 42a and the filter line 42c at least partially extend in parallel. The second line 42b is formed in a straight line and is connected in series to a part of the first line 42a extending in parallel with the filter line 42c. At least a part of the first line 42a extends between the second line 42b and the filter line 42c extending in parallel. Each of the first coupling portion 48, the second coupling portion 50, and the third coupling portion 51 is included in a part of the flow path 42.

In the cassette body 40, a seal portion 55 corresponding to a welding position is formed on both sides of the flow path 42 along the flow path 42. In addition, a seal portion 57 is formed on an outer peripheral edge 40c of the cassette body 40 along the outer peripheral edge 40c. In the cassette body 40 (excluding a convex portion forming the flow path 42), a position other than the seal portions 55 and 57 corresponds to a non-sealed portion in which the first sheet 40a and the second sheet 40b are not welded to each other.

The first coupling portion 48 is included in a branch portion that branches one fluid passage 61a into two fluid passages 61b and 61e and is included in a merging portion that merges the two fluid passages 61b and 61e into the one fluid passage 61a. The second coupling portion 50 is included in a merging portion that merges two fluid passages 61c and 61e to one fluid passage 61d and is included in a branch portion that branches the one fluid passage 61d into the two fluid passages 61c and 61e.

The first coupling portion 48 is configured such that a change in flow direction of a fluid in the first coupling portion 48 corresponds to an obtuse angle. Specifically, one end side 42a1 of the first line 42a is connected to the filter line 42c so as to be inclined toward the second end 45b side of the cassette body 40.

The second coupling portion 50 is configured such that a change in flow direction of a fluid in the second coupling portion 50 corresponds to an obtuse angle. Specifically, the other end side 42a2 of the first line 42a is connected to the filter line 42c so as to be inclined toward the first end 45a side of the cassette body 40.

The third coupling portion 51 is configured such that a change in flow direction of a fluid in the third coupling portion 51 corresponds to an obtuse angle. Specifically, the fluid passage 61c is connected to the fluid passage 61b so as to be inclined toward the second end 45b side of the cassette body 40.

As described above, according to the cassette 28B, each of the first coupling portion 48, the second coupling portion 50, and the third coupling portion 51 is configured such that a change in flow direction of a fluid in the coupling portion corresponds to an obtuse angle. According to this configuration, it is possible to reduce damage to blood when blood flows through each coupling portion.

The flow path diameter of the first coupling portion 48 is smaller than the flow path diameter of the line adjacent to the first coupling portion 48. The flow path diameter of the second coupling portion 50 is smaller than the flow path diameter of the line adjacent to the second coupling portion 50. The flow path diameter of the third coupling portion 51 is smaller than the flow path diameter of the line adjacent to the third coupling portion 51. That is, the first coupling portion 48, the second coupling portion 50, and the third coupling portion 51 are configured to be thinner than the other lines in the flow path 42. According to this configuration, the flow paths of the first coupling portion 48, the second coupling portion 50, and the third coupling portion 51 may be inhibited from being crushed.

Figure 14:
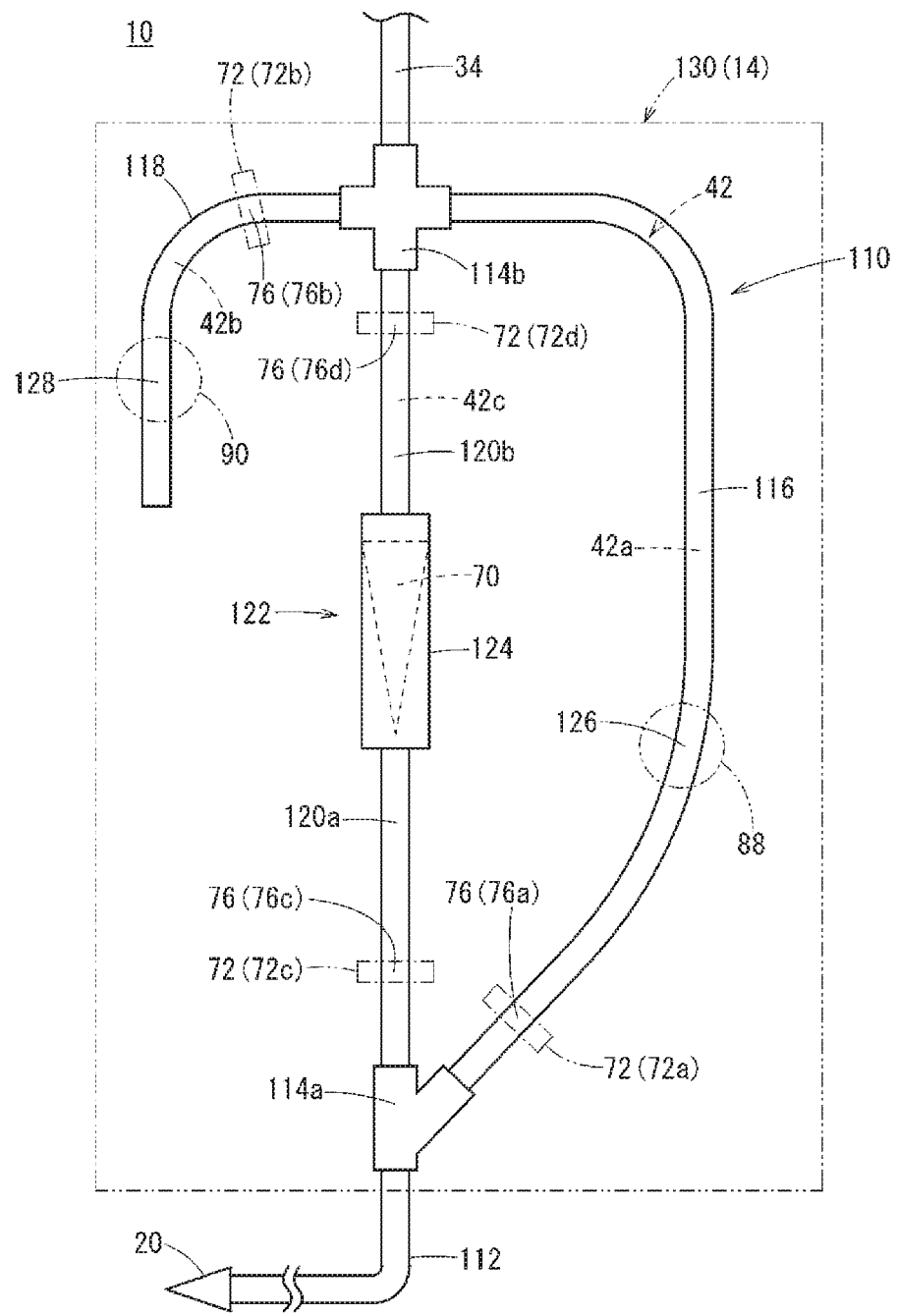
FIG. 14 is a schematic view of a blood component collection kit.

In the blood component collection system 10 described above, a blood component collection kit 110 (hereinafter abbreviated to a "kit 110") illustrated in FIG. 14 may be adopted instead of the cassette 28. In the kit 110, the same or equivalent constituent elements as those of the cassette 28 are denoted by the same reference numerals. In the kit 110, a member forming the flow path 42 in the cassette 28 includes only a tube.

Specifically, the kit 110 includes a blood collection needle 20 for collecting blood from the donor, a blood collection tube 112 having one end connected to the blood collection needle 20, a first tube 116 (first line forming member) connected to the blood collection tube 112 via a tube connector 114a, and a second tube 118 (second line forming member) connected to the first tube 116 via a tube connector 114b. The kit 110 further includes a first filter line tube 120a connected to the blood collection tube 112 and the first tube 116 via the tube connector 114a, a second filter line tube 120b connected to the first tube 116 and the second tube 118 via the tube connector 114b, and a filter mechanism 122 having both ends connected to the first filter line tube 120a and the second filter line tube 120b.

The blood collection tube 112, the first tube 116, the second tube 118, the first filter line tube 120a, and the second filter line tube 120b are made of a soft material. One end of the processing unit-side tube 34 is connected to the tube connector 114b. The other end of the processing unit-side tube 34 is connected to the blood processing unit 16 (see FIG. 1). The filter mechanism 122 has the filter member 70 for removing blood clumps contained in blood or blood components, and a housing 124 for accommodating the filter member 70.

A flow path in the first tube 116 is included in the first line 42a. A flow path in the second tube 118 is included in the second line 42b. For example, an end of the second tube 118 opposite to an end connected to the tube connector 114b is sealed by a tube sealer, etc. At the time of blood collection, blood from the donor is sent to the first line 42a, and the second line 42b is filled with air. A flow path in the first filter line tube 120a, a flow path in the second filter line tube 120b, and a flow path in the housing 124 are included in the filter line 42c.

The first tube 116 is provided with a first pressure-receiving portion 126 pressed by the first load detector 88 in a kit attached state in which the kit 110 is attached to the centrifugal separator 14. The second tube 118 is provided with a second pressure-receiving portion 128 pressed by the second load detector 90 in the kit attached state. The first pressure-receiving portion 126 and the second pressure-receiving portion 128 are formed to have the same shape and size. Therefore, the first pressure-receiving portion 126 and the second pressure-receiving portion 128 have the same rigidity. The first pressure-receiving portion 126 and the second pressure-receiving portion 128 may have shapes similar to those of the first pressure-receiving portion 60 and the second pressure-receiving portion 62 illustrated in FIG. 2, etc.

The kit 110 is provided with a plurality of clamping action portions 76 (76a to 76d) on which a plurality of clamps 72 (72a to 72d) included in the centrifugal separator 14 acts. When the kit 110 is used, the centrifugal separator 14 is provided with a kit attaching portion 130 in place of the cassette attaching portion 78 (FIG. 1). Although details are omitted, the kit attaching portion 130 has an attachment base on which a mounting groove allowing the kit 110 to be mounted therein is formed and a lid body that can be opened and closed with respect to the attachment base, and is configured such that the kit 110 is interposed between the attachment base and the lid body when the lid body is closed.

The plurality of clamps 72 (72a to 72d) is disposed according to arrangement of the plurality of clamping action portions 76 (76a to 76d). When the kit 110 is attached to the centrifugal separator 14, the clamping action portions 76 abut on or face the corresponding clamps 72. The clamp 72a can press the first tube 116. The clamp 72b can press the second tube 118. The clamp 72c can press the first filter line tube 120a. The clamp 72d can press the second filter line tube 120b.

When the kit 110 configured as described above is used, similarly to the case of using the cassette 28 illustrated in FIG. 2, etc., it is possible to accurately measure the circuit internal pressure (negative pressure and positive pressure) based on the load detected by the first load detector 88 of the centrifugal separator 14 and the load detected by the second load detector 90.

The present invention is not limited to the above-described embodiments, and can be variously modified within a range not departing from a subject matter of the present invention.

REFERENCE SIGNS LIST

10 Blood component collection system
14 Centrifugal separator
28, 28A, 28B Blood component collection cassette
42 Flow path
42a First line
42b Second line
54 First line forming member
56 Second line forming member
88 First load detector
90 Second load detector
110 Blood component collection kit

The invention claimed is:

1. A blood component collection cassette comprising a cassette body in which a flow path is formed,
wherein the blood component collection cassette is configured to be attachable to a blood component separation device having, for load detection, a first load detector and a second load detector,
the flow path has a first line through which blood flows when the blood component separation device is in operation and a second line through which blood does not flow when the blood component separation device is in operation,
the cassette body includes a first line forming member made of a soft material to form the first line and a second line forming member made of a soft material to form the second line,
the first line forming member is provided with a first pressure-receiving portion to be pressed by the first load detector in an attached state in which the blood component collection cassette is attached to the blood component separation device, and
the second line forming member is provided with a second pressure-receiving portion to be pressed by the second load detector in the attached state.

2. The blood component collection cassette according to claim 1, wherein the cassette body has a first sheet and a second sheet, which are made of a soft material, the first sheet and the second sheet are overlapped in a thickness direction and coupled to each other, and the flow path is formed between the first sheet and the second sheet.

3. The blood component collection cassette according to claim 1, wherein the first line and the second line communicate with each other.

4. The blood component collection cassette according to claim 1, wherein the first pressure-receiving portion and the second pressure-receiving portion are formed in a same shape.

5. The blood component collection cassette according to claim 1, wherein at least the first pressure-receiving portion and the second pressure-receiving portion form open flow paths in a natural state in which the cassette body is not elastically deformed.

6. The blood component collection cassette according to claim 1,
wherein at least one of the first line forming member and the second line forming member has a standard portion having a relatively small flow path width and a wide portion having a larger flow path width than the flow path width of the standard portion, and
the wide portion is included in the first pressure-receiving portion or the second pressure-receiving portion.

7. The blood component collection cassette according to claim 1, wherein the cassette body has a cassette base portion made of a hard material, the cassette base portion supporting the first line forming member and the second line forming member.

8. The blood component collection cassette according to claim 7, wherein the second line is a fluid flow path independent of and non-communicating with the first line.

9. The blood component collection cassette according to claim 1 wherein said first line is fluidly connected in parallel with a filter.

10. The blood component cassette according to claim 1 wherein said second line is in fluid communication with said first line at a first end and is closed at a second end.

11. The blood component cassette according to claim 10 wherein said first end of said second line is connected to said first line downstream from said first pressure-receiving portion.

12. A blood component collection system comprising:
a blood component separation device having a first load detector and a second load detector; and
a blood component collection cassette configured to be attachable to the blood component separation device,
wherein the blood component collection cassette includes a cassette body in which a flow path is formed,
the flow path has a first line through which blood flows when the blood component separation device is in operation and a second line through which blood does not flow when the blood component separation device is in operation,
the cassette body includes a first line forming member made of a soft material to form the first line and a second line forming member made of a soft material to form the second line,
the first line forming member is provided with a first pressure-receiving portion to be pressed by the first load detector in an attached state in which the blood component collection cassette is attached to the blood component separation device,
the second line forming member is provided with a second pressure-receiving portion to be pressed by the second load detector in the attached state, and
the blood component separation device obtains an internal pressure of the first line based on a load detected by the first load detector and a load detected by the second load detector.

13. The blood component collection system according to claim 12, wherein the cassette body has a first sheet and a second sheet, which are made of a soft material, the first sheet and the second sheet are overlapped in a thickness direction and coupled to each other, and the flow path is formed between the first sheet and the second sheet.

14. The blood component collection system according to claim 12, wherein the first line and the second line communicate with each other through a flow path, and the blood component separation device includes a clamp allowed to press the cassette body to block the flow path between the first line and the second line.

15. The blood component collection system according to claim 12, wherein the first pressure-receiving portion and the second pressure-receiving portion are formed in a same shape.

16. The blood component collection system according to claim 12, wherein at least one of the first line forming member and the second line forming member has a standard portion having a relatively small flow path width and a wide portion having a larger flow path width than the flow path width of the standard portion, and the wide portion is included in the first pressure-receiving portion or the second pressure-receiving portion.

17. The blood component collection system according to claim 12 wherein said first line is fluidly connected in parallel with a filter.

18. The blood component collection system according to claim 12 wherein said second line is in fluid communication with said first line at a first end and is closed at a second end.

19. The blood component collection system according to claim 18 wherein said first end of said second line is connected to said first line downstream from said first pressure-receiving portion.

20. A blood component collection kit configured to be attached to a blood component separation device having a first load detector and a second load detector, the blood component collection kit comprising:

a blood collection needle for collecting blood from a donor; and a flow path member in which a flow path is formed to connect the blood collection needle and a centrifugal unit of the blood component separation device to each other, wherein the flow path comprises a cassette comprising a first line and a second line branching from the first line, the first line is supplied with the blood collected from the donor, the second line is filled with air, the flow path member has a first line forming member made of a soft material to form the first line and a second line forming member made of a soft material to form the second line, the first line forming member is provided with a first pressure-receiving portion configured to be pressed by the first load detector of the blood component separation device in an attached state in which the blood component collection kit is attached to the blood component separation device, and the second line forming member is provided with a second pressure-receiving portion configured to be pressed by the second load detector of the blood component separation device in the attached state.

21. A flow path internal pressure detection method of detecting a pressure in a flow path of a blood component collection cassette attached to a blood component separation device for collecting a blood component, the blood component collection cassette including a cassette body in which a flow path is formed, the flow path having a first line and a second line, the cassette body having a first line forming member made of a soft material to form the first line and a second line forming member made of a soft material to form the second line, the flow path internal pressure detection method comprising:

a first measurement step of pressing the first line forming member in a state in which blood is sent to the first line and measuring a load $\alpha 1$ caused by pressing of the first line forming member;

a second measurement step of pressing the second line forming member in a state in which blood is not sent to the second line and measuring a load $\alpha 2$ caused by pressing of the second line forming member;

a load calculation step of calculating a differential load $\alpha$ obtained by subtracting the load $\alpha 2$ measured in the second measurement step from the load $\alpha 1$ measured in the first measurement step; and an internal pressure calculation step of calculating an internal pressure of the first line based on the calculated differential load $\alpha$.

* * * * *